US012589081B2

(12) United States Patent
Acharya et al.

(10) Patent No.: US 12,589,081 B2
(45) Date of Patent: Mar. 31, 2026

(54) CURCUMIN COMPOSITIONS FOR OSTEOARTHRITIS AND JOINT WELLNESS

(71) Applicant: OmniActive Health Technologies Limited, Mumbai (IN)

(72) Inventors: Manutosh Acharya, Thane (IN); Prafull Dutt Singh, Thane (IN); Prakash Bhanuse, Thane (IN)

(73) Assignee: OmniActive Health Technologies Limited, Mumbai (IN)

( * ) Notice: Subject to any disclaimer, the term of this patent is extended or adjusted under 35 U.S.C. 154(b) by 707 days.

(21) Appl. No.: 17/778,953

(22) PCT Filed: Dec. 2, 2020

(86) PCT No.: PCT/IB2020/061351
§ 371 (c)(1),
(2) Date: May 23, 2022

(87) PCT Pub. No.: WO2021/111312
PCT Pub. Date: Jun. 10, 2021

(65) Prior Publication Data
US 2023/0241006 A1      Aug. 3, 2023

(30) Foreign Application Priority Data

Dec. 3, 2019      (IN) .............................. 201921049620

(51) Int. Cl.
*A61K 31/12*          (2006.01)
*A61K 47/06*          (2006.01)
(Continued)

(52) U.S. Cl.
CPC .............. *A61K 31/12* (2013.01); *A61K 47/06* (2013.01); *A61K 47/12* (2013.01); *A61K 47/14* (2013.01);
(Continued)

(58) Field of Classification Search
CPC ........ A61K 31/12; A61K 47/06; A61K 47/22; A61P 19/02
See application file for complete search history.

(56) References Cited

U.S. PATENT DOCUMENTS

| | | | |
|---|---|---|---|
| 8,785,380 B2 | 7/2014 | Madhavamenon et al. | |
| 2014/0010903 A1 | 1/2014 | Madhavamenon et al. | |
| 2014/0271530 A1 | 9/2014 | Tummala et al. | |

FOREIGN PATENT DOCUMENTS

| | | |
|---|---|---|
| CN | 107308133 | 11/2017 |
| JP | 2011068680 | 4/2011 |

(Continued)

OTHER PUBLICATIONS

Search Strategy dated Oct. 6, 2021 in the file history of the corresponding international application.
(Continued)

*Primary Examiner* — San Ming R Hui
(74) *Attorney, Agent, or Firm* — Hoxie & Associates LLC

(57)          ABSTRACT
The present invention relates to a stable curcumin composition for prevention improvement and maintenance of arthritis more particularly to osteoarthritis. The stable curcumin composition is comprised of curcuminoids either alone or along with at least one pharmaceutically and/or nutraceutically accepted excipient to form the stable curcumin compositions having enhancement in absorption and bioavailability. The composition is safe for consumption, possess enhanced stability and bioavailability due to selective percentage of amorphous and crystalline polymorphic form of curcumin along with selective excipient such as pH modifier and/or stabilizer and optionally hydrophilic carrier, antioxidant, diluents, anticaking agent, emulsifier, fat and surfactant which result in improvement of symptoms of arthritis and associated conditions, when administered to subjects, in need thereof.

20 Claims, 9 Drawing Sheets

| % Crystallinity | % Amorphous |
|---|---|
| 1.20% | 98.80% |

(51) Int. Cl.

| | | |
|---|---|---|
| *A61K 47/12* | (2006.01) | |
| *A61K 47/14* | (2017.01) | |
| *A61K 47/20* | (2006.01) | |
| *A61K 47/22* | (2006.01) | |
| *A61K 47/24* | (2006.01) | |
| *A61K 47/38* | (2006.01) | |
| *A61P 19/02* | (2006.01) | |

(52) U.S. Cl.

CPC .............. *A61K 47/20* (2013.01); *A61K 47/22* (2013.01); *A61K 47/24* (2013.01); *A61K 47/38* (2013.01); *A61P 19/02* (2018.01)

(56) References Cited

FOREIGN PATENT DOCUMENTS

| | | |
|---|---|---|
| JP | 2017516764 | 6/2017 |
| JP | 2019151584 | 9/2019 |
| KR | 20170076496 | 7/2017 |
| WO | 2007/103435 | 9/2007 |
| WO | WO 2012049253 A1 | 4/2012 |
| WO | 2012138907 | 10/2012 |
| WO | 2012/156979 | 11/2012 |
| WO | 2013/122988 | 8/2013 |
| WO | 2017/175077 | 10/2017 |
| WO | WO 2018211380 A1 | 11/2018 |
| WO | 2019/160146 | 8/2019 |

OTHER PUBLICATIONS

International Search Report dated Oct. 6, 2021.

Written Opinion of the International Searching Authority dated Oct. 6, 2021.

Chin, Kok-Yong. "The spice for joint inflammation : . . . curcumin in treating osteoarthritis." Drug Design, Development and Therapy 10(2016):3029-3042.

Aditya et al., "Amorphous nano-curcumin stabilized oil in water emulsion: Physico chemical characterization", Food Chemistry, Elsevier Ltd, NL, vol. 224, Dec. 23, 2016, pp. 191-200.

Mahmood et al., "Enhancement of bioactivity and bioavailability of curcumin with chitosan based materials", Korean Journal of Chemical Engineering, vol. 33, No. 12, Oct. 13, 2016, pp. 3316-3329.

Wegiel et al., "Curcumin amorphous solid dispersions: the influence of intra and intermolecular bonding on physical stability", Pharmaceutical Development and Technology, vol. 19, No. 8, Jan. 1, 2014, pp. 976-986.

Mun, et al., "Oral Administration of Curcumin Suppresses Production of Matrix Metalloproteinase (MMP)-1 and MMP-3 to Ameliorate Collagen-Induced Arthritis: Inhibition of the PKCo/JNK/c-Jun Pathway" Journal of Pharmacological Sciences, 2009, 111, 13-21.

Figure 01: X-ray diffraction (XRD) graph of the composition prepared as per example 01
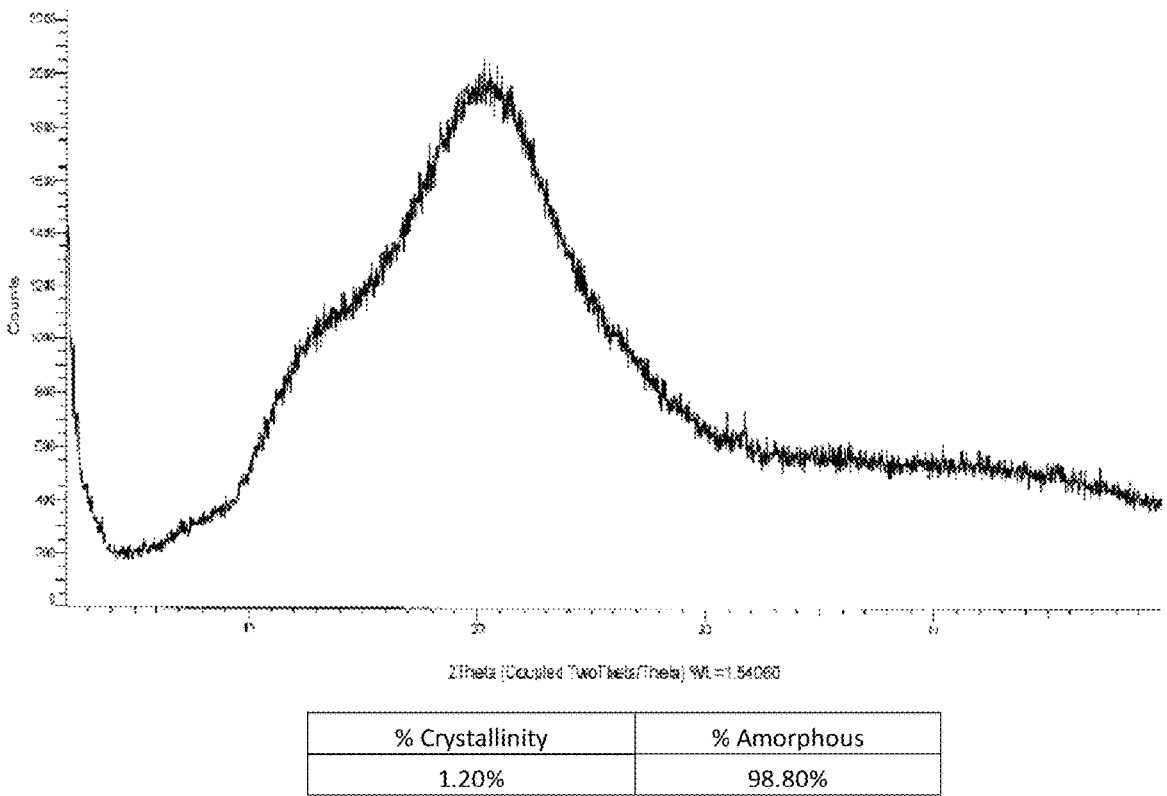
| % Crystallinity | % Amorphous |
|---|---|
| 1.20% | 98.80% |
Figure 02: X-ray diffraction of powder (XRD) graph of the composition prepared as per example 02
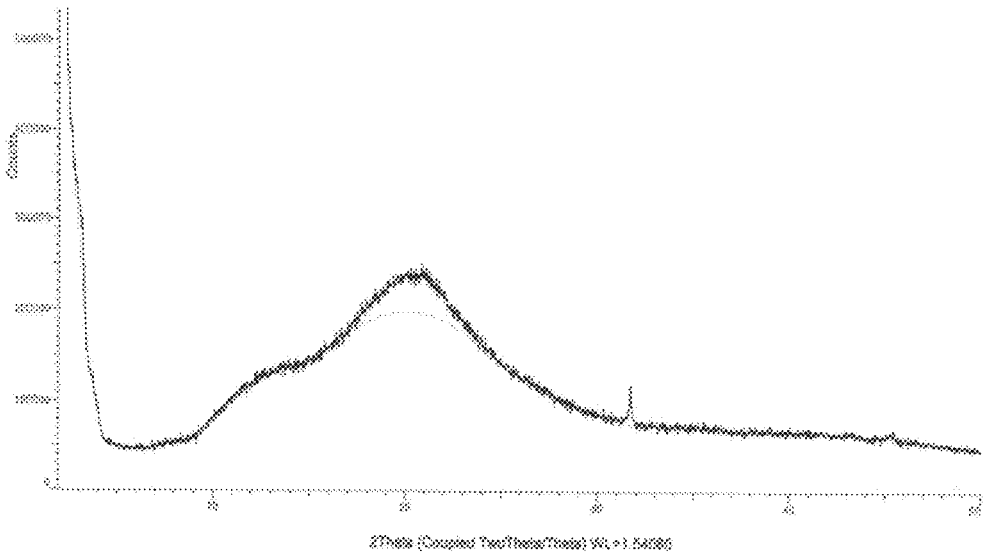
| % Crystallinity | % Amorphous |
|---|---|
| 1.20% | 98.80% |

Figure 03: X-ray diffraction (XRD) graph of the composition prepared as per example 03
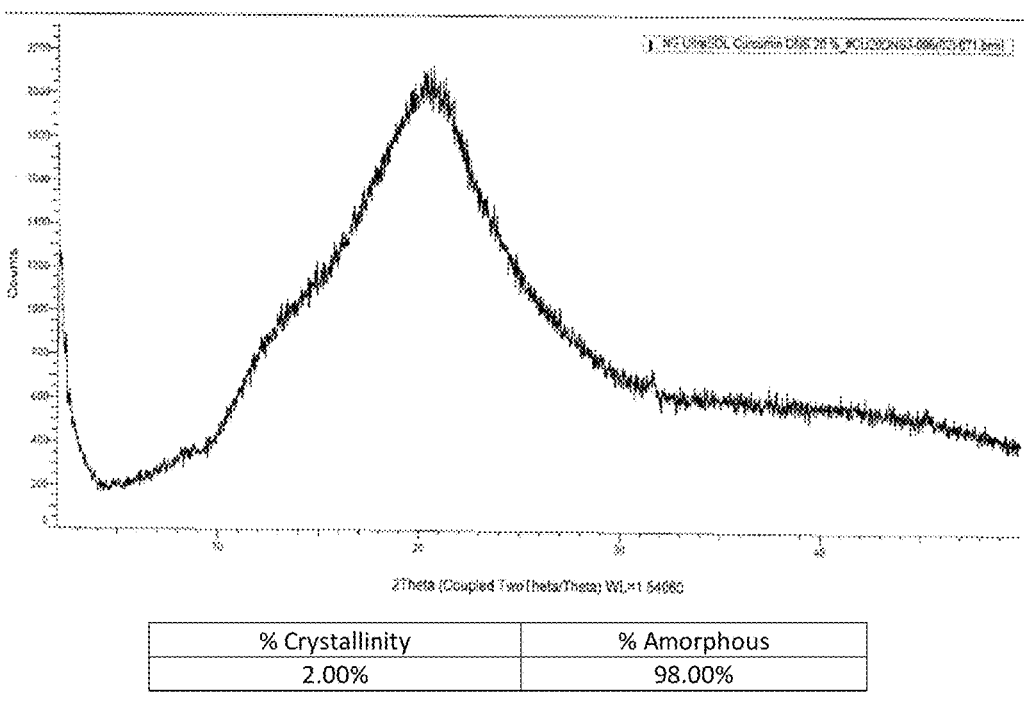
| % Crystallinity | % Amorphous |
|---|---|
| 2.00% | 98.00% |
Figure 04: X-ray diffraction (XRD) graph of the composition prepared as per example 04
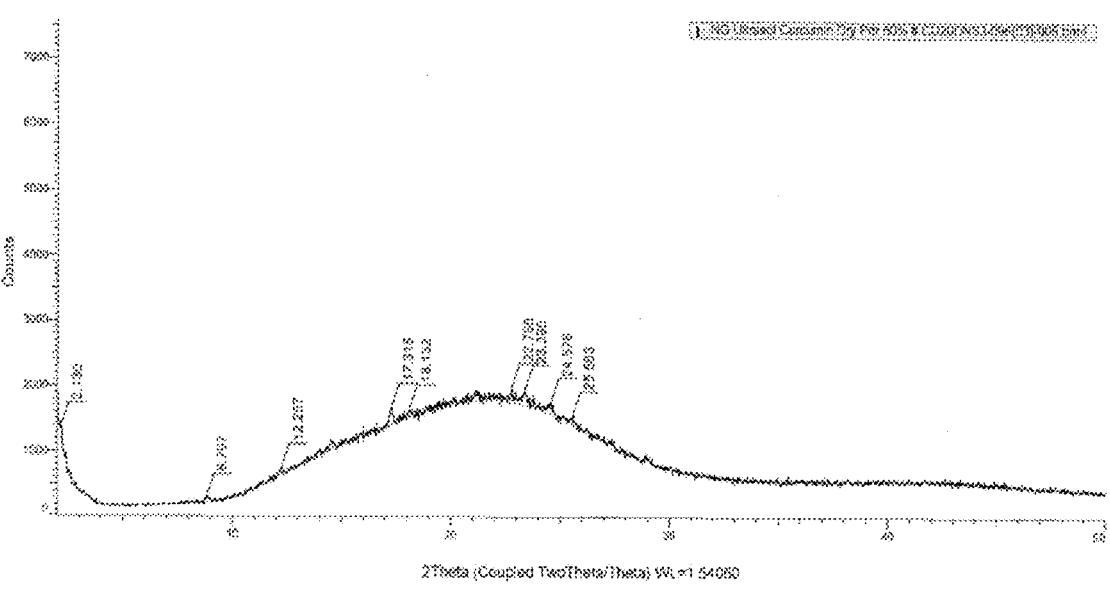
| % Crystallinity | % Amorphous |
|---|---|
| 4.00% | 96.00% |

Figure 5. Effects of curcumin (Cur) on knee joint protein expression of IL-β (A), IL-6 (B), TNF-α (C) and NF-κβ (D) levels in monosodium iodoacetate (MIA) induced osteoarthritis (OA) rats.
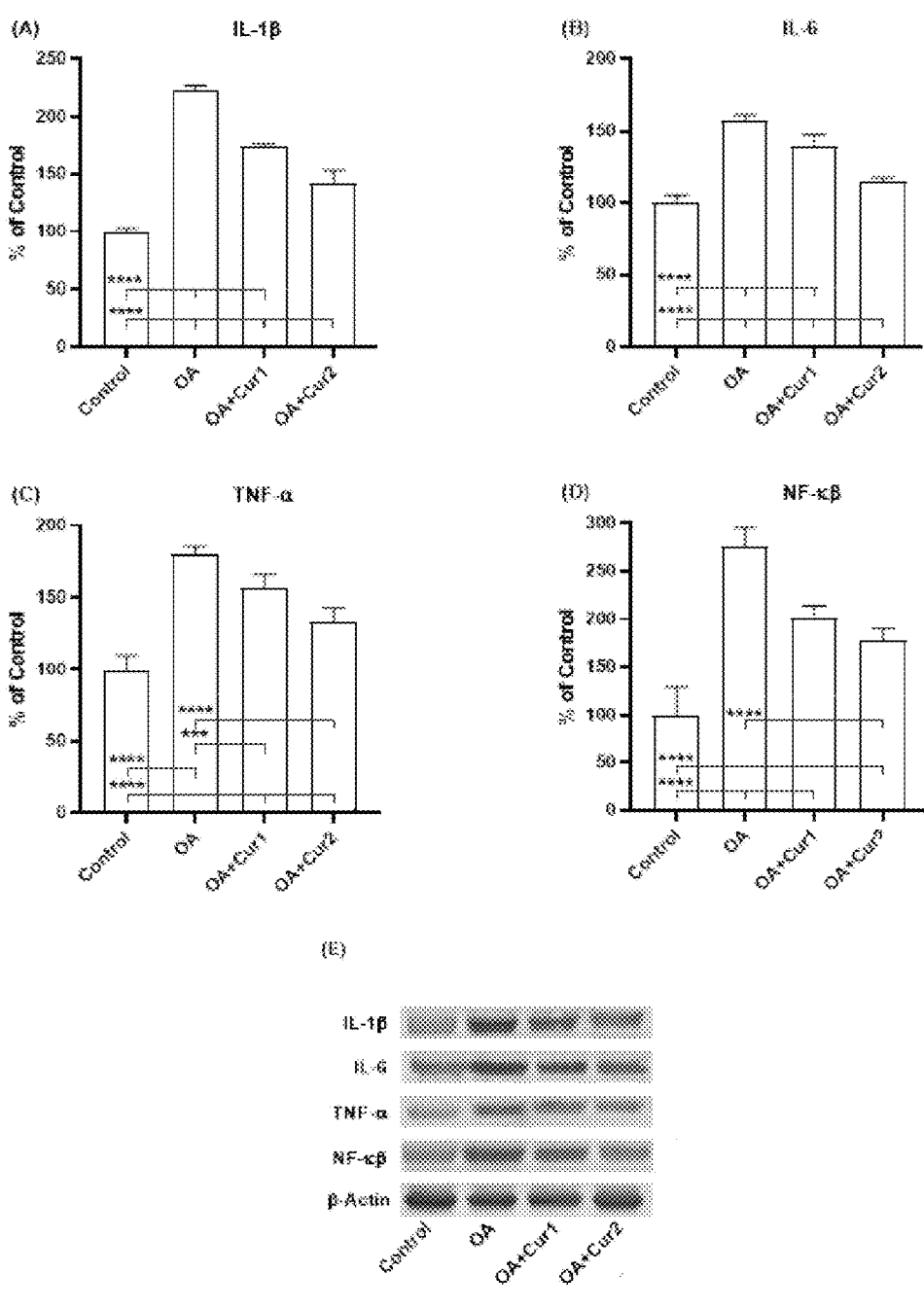

Figure 6: Effects of curcumin (Cur) on knee joint protein expression of collagen type 2 (A), MMP-3 (B), COX-2 (C) and LOX-5 (D) levels in monosodium iodoacetate (MIA) induced osteoarthritis (OA) rats.
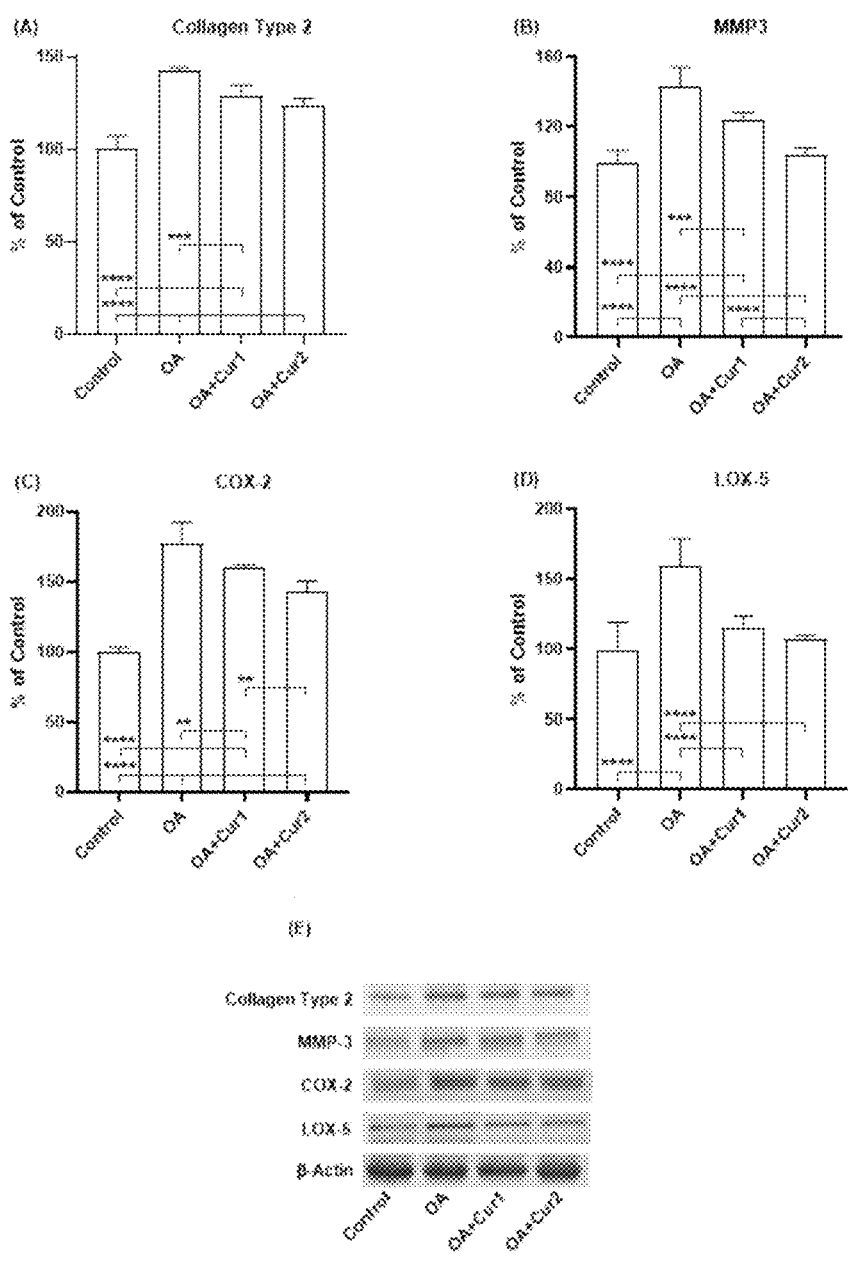

Figure 7.Effects of curcumin (Cur) on the knee joint in monosodium iodoacetate (MIA) induced osteoarthritis (OA) rats.
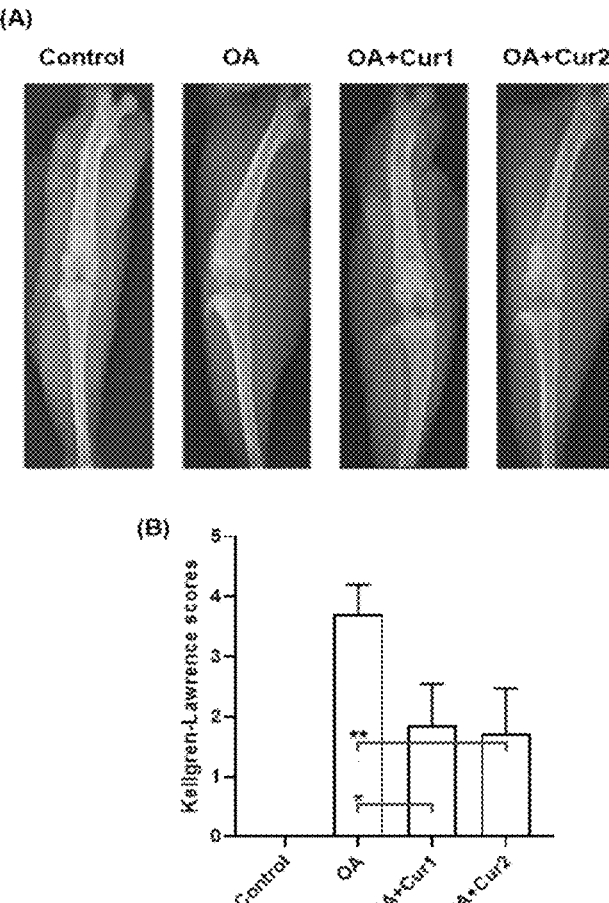

Figure 8.Effects of curcumin (Cur) on histopathology of the knee joint in monosodium iodoacetate (MIA) induced osteoarthritis (OA) rats.
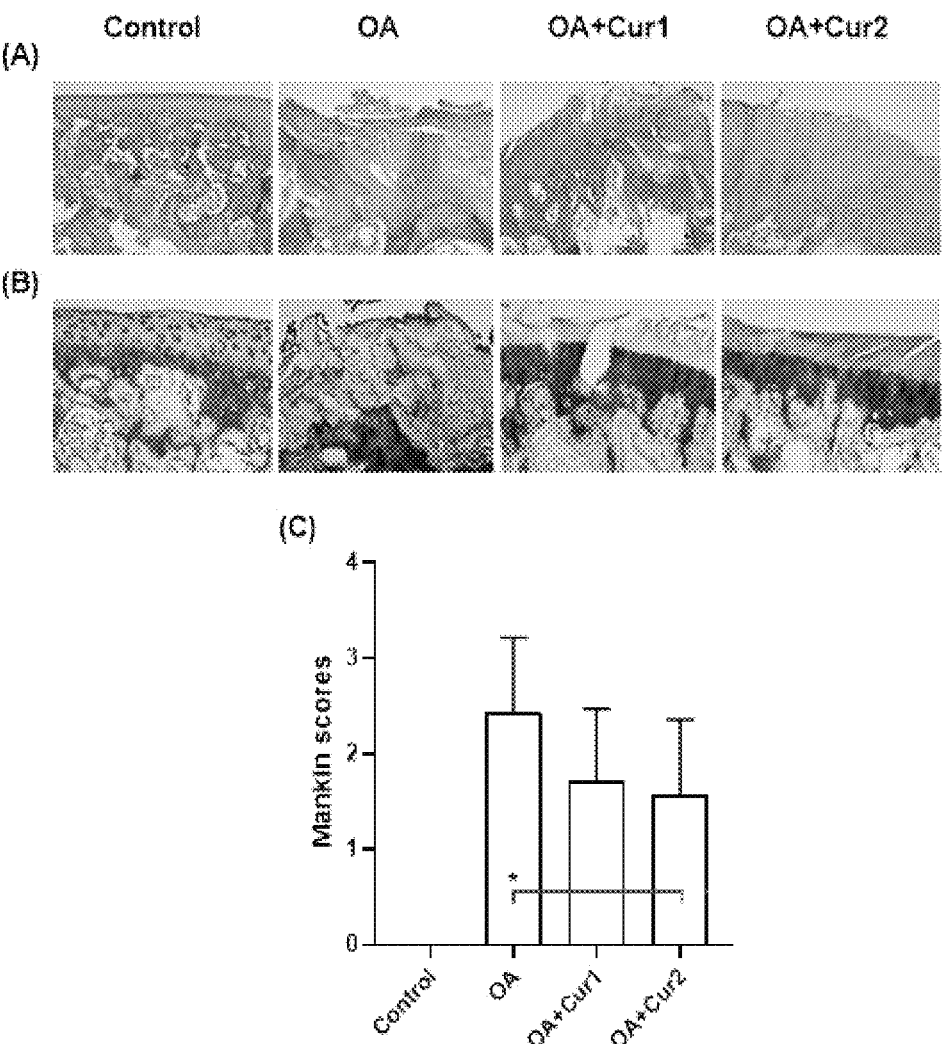

Figure 9. Effects of curcumin (Cur) on knee swelling (A), left knee joint diameter (B) right knee joint diameter (C) and the ratio of right to left diameter values (D) in monosodium iodoacetate (MIA) induced osteoarthritis (OA) rats.
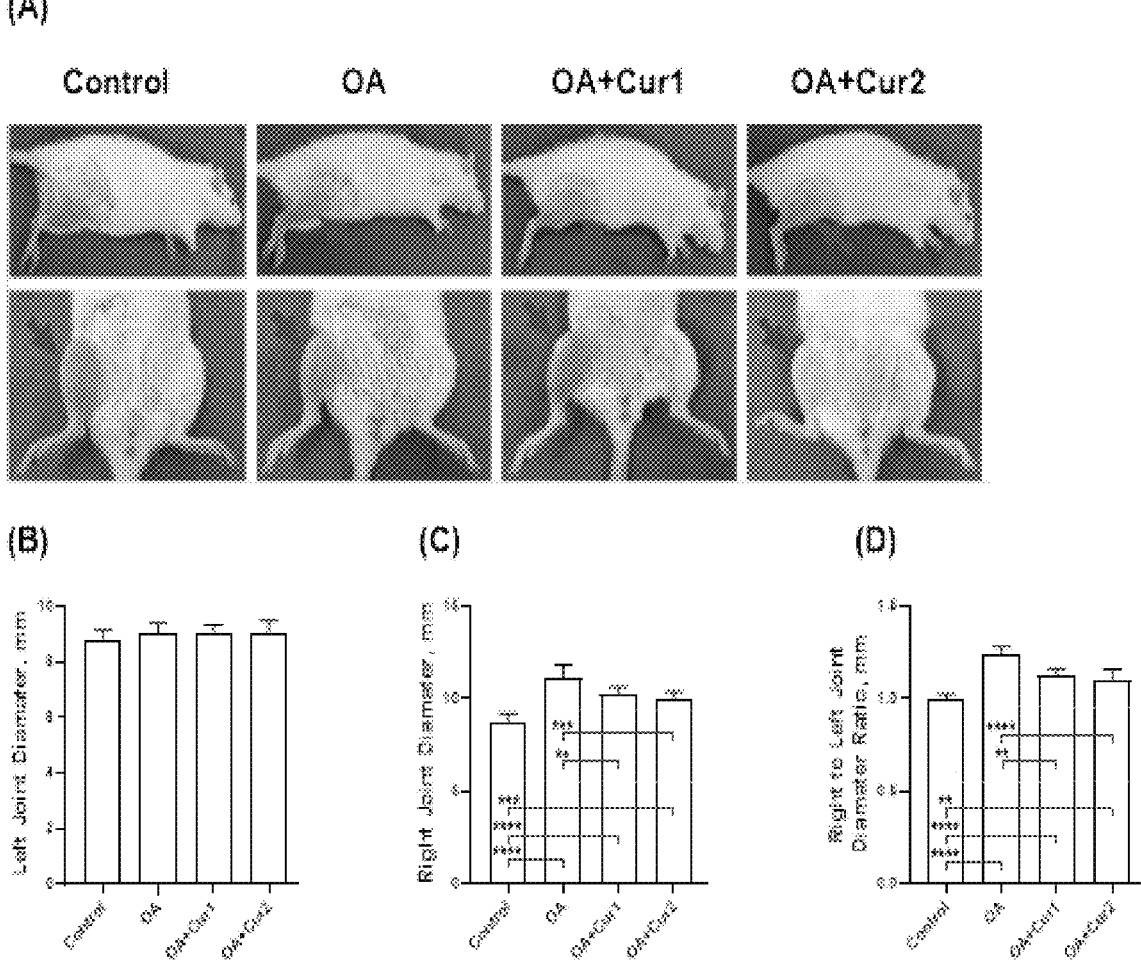

Figure 10. Effects of curcumin (Cur) on paw area (B) and stride length (D) in monosodium iodoacetate (MIA) induced osteoarthritis (OA) rats.
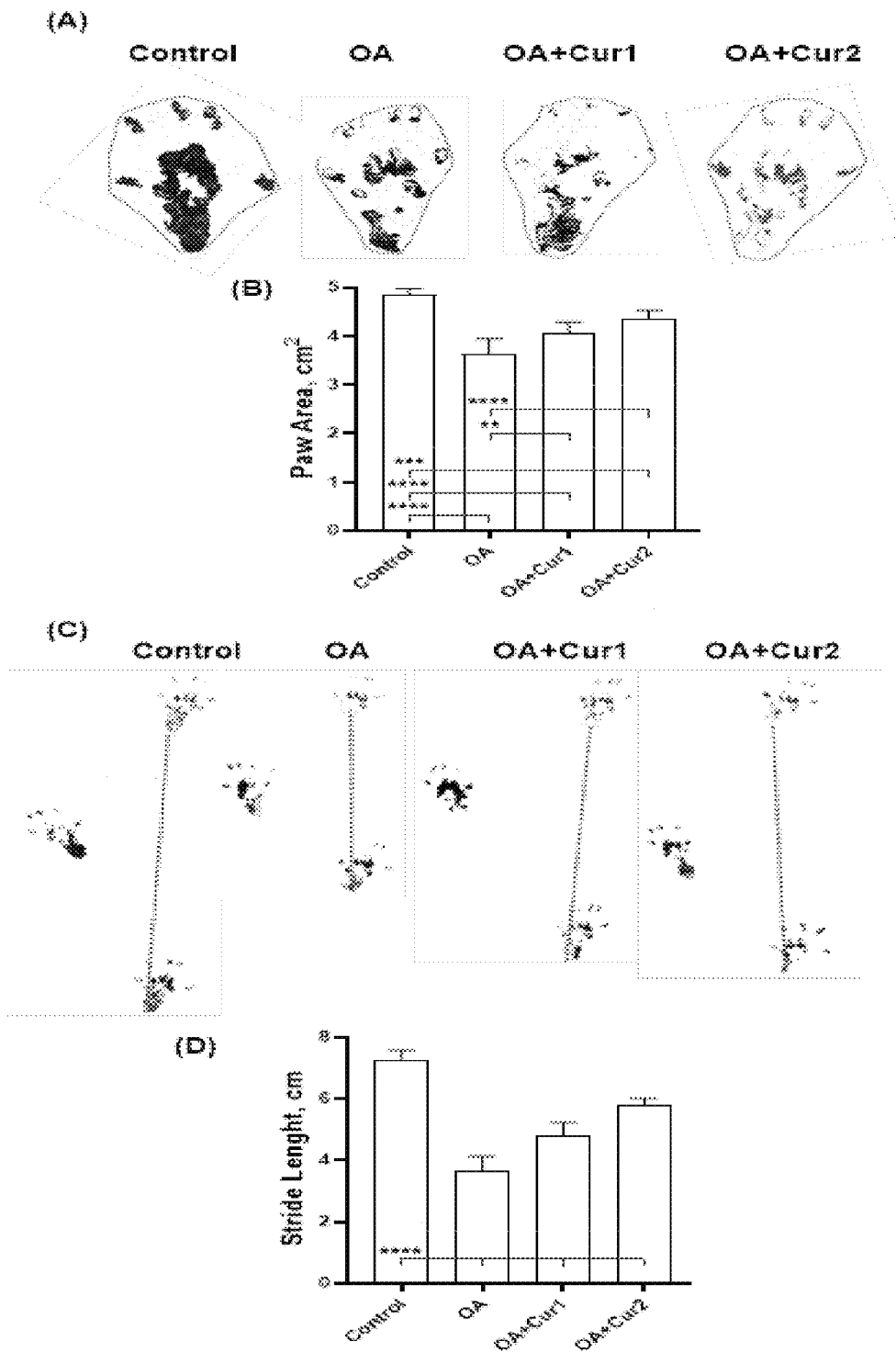

Figure 11: Plasma total curcuminoids concentration of Curcumin composition vs Reference
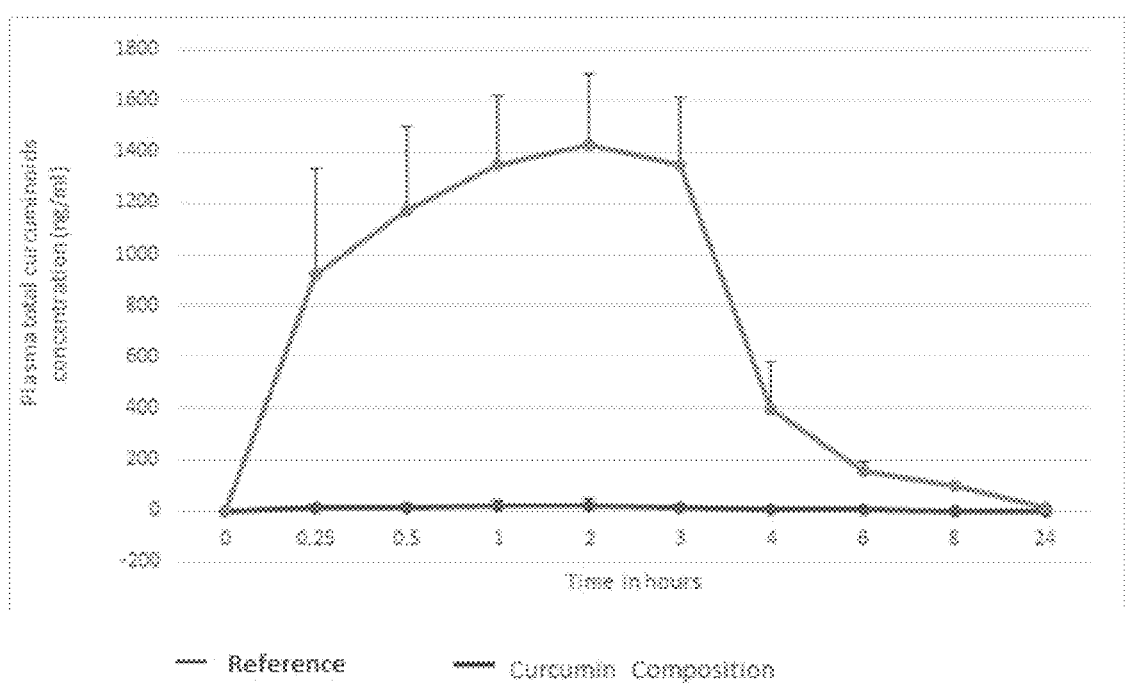

CURCUMIN COMPOSITIONS FOR OSTEOARTHRITIS AND JOINT WELLNESS

CROSS REFERENCE TO RELATED APPLICATIONS

This patent application is a U.S. National Stage application of International Patent Application Number PCT/IB2020/061351, filed on Dec. 3, 2020, which claims the benefit of priority of Indian patent application number IN201921049620, filed on Dec. 3, 2019, which is incorporated herein by reference in its entirety.

FIELD OF THE PRESENT INVENTION

The present invention is related to the stable curcumin composition for prevention, improvement and maintenance of arthritis more particularly to osteoarthritis. More specifically stable curcumin compositions comprising curcuminoids in different polymorphic forms like amorphous and crystalline and/or in selective ratio and improved the stability of curcumin in alkaline pH environment of the intestine for enhancement in bioavailability.

BACKGROUND OF THE PRESENT INVENTION

Arthritis is a more specific term that implies damage or inflammation in one or more joints. The condition is often manifested by pain, swelling, heat, redness and limitation of movement. Knee osteoarthritis is a type of disease that results from the degradation of articular cartilage between the bones. As a result of this reduction in cartilage, there is more friction between the bones and results in painful bone spurs.

Curcumin is derived from the rhizome of *Curcuma longa* and has been traditionally used in the treatment of inflammation, skin wounds, tumors etc. Overall, curcumin is associated with several health claims, but its therapeutic use is limited due to its low bioavailability, poor aqueous solubility, instability at neutral and basic pH, poor absorption, rapid metabolism, and short half-life. Curcumin is a class IV drug (low solubility and low permeability) based on the bio pharmaceutics classification system (BCS). Many strategies have been developed to overcome these limitations, particularly for oral delivery systems.

US2016089343A1 disclosed herein are formulations for the local delivery of therapeutically effective doses of curcumin that provide sufficient serum levels of curcumin to treat diseases such as head and neck disorders and upper aerodigestive disorders.

EP3275430A1 relates to an aqueous solution for intravenous infusion containing curcumin and/or one or more curcumin derivatives, dimethylsulfoxide, one or more solubilizers, sodium selenite, a buffer in an aqueous infusion medium, as well as a concentrate containing for their preparation curcumin and/or one or more curcumin, dimethyl sulfoxide, one or more solubilizing agents and sodium selenite.

In K.N. Pushpakumari International journal of pharmaceutical sciences and research an impact factor (2019): 1.230 cite score (2017): 0.27), The comparative data of bioabsorption of two turmeric formulations containing curcuminoids in a varied composition compared to regular turmeric extract. The document is completely silent over the effect of curcumin on osteoarthritis.

In order to find a satisfactory solution to the persisting problem, there is a strong felt need to develop the stable curcumin formulation for treatment, prevention and maintenance of arthritis more specifically to osteoarthritis. The stable curcumin compositions comprising curcuminoids in different polymorphic forms like amorphous and crystalline and/or in selective ratio for enhancement in bioavailability. The stable curcumin composition is comprised of curcuminoids either alone or along with at least one pharmaceutically and/or nutraceutically accepted excipient to form stable curcumin compositions having enhanced absorption and bioavailability.

OBJECTIVES OF THE PRESENT INVENTION

The main objective of the present invention is to develop stable curcumin formulation for prevention, improvement and maintenance of arthritis.

Another objective of the present invention is to provide the stable curcumin formulation having enhancement in bioavailability which is available in an orally administered form.

Another objective of the present invention is to develop the stable curcumin formulation comprising curcuminoids in different polymorphic form like amorphous and crystalline and/or in selective ratio for enhancement in absorption and bioavailability.

Another objective of the present invention is to develop the stable curcumin formulation comprising curcuminoids either alone and/or along with at least one pharmaceutically and/or nutraceutically accepted excipient to form stable curcumin compositions having enhancement in absorption and bioavailability.

Another objective of the present invention is to develop the stable curcumin formulation comprising of curcuminoids either alone and/or along with at least one pH modifier and stabilizer optionally with hydrophilic carrier, antioxidant, diluents, anticaking agent, emulsifier, fat and surfactant to form stable curcumin compositions having enhancement in absorption and bioavailability.

Further aspect of the present invention is to provide a process for preparation of the stable curcumin composition suitable for formulating into tablets, capsules, blended powders, licaps, ointments, pastes, lotions, liniments, mouthwashes, gargles, consumable dry syrups, liquid syrups, health drinks, diet drinks, fruit juices, soft drinks and the like.

One more objective of the present invention is to provide stable curcumin compositions, use for prevention, improvement and maintenance arthritis more particularly to osteoarthritis and its associated conditions like articulate cartilage, joint mobility, joint flexibility, reduction in joint stiffness and reduction in inflammation.

Further objective of the present invention is to provide stable curcumin compositions, use for improvement in muscle strength and muscle performance, reduction in muscle soreness and muscle damage and promote faster muscle recovery.

SUMMARY OF THE PRESENT INVENTION

According to an aspect of the present invention there is provided a stable curcumin composition having enhanced bioavailability comprising;

i) Curcumin containing crystalline polymorphic form of curcuminoids in the range of 0 to 15% and amorphous polymorphic form of curcuminoids in the range of 85 to 100% and ii) At least one or more pharmaceutically or nutraceutically accepted ingredient selected from hydrophilic carrier, antioxidant, stabilizer, pH Modifier, solubilizer, fat, anticaking agent

BRIEF DESCRIPTION OF THE ACCOMPANYING FIGURES

FIG. 1: X-ray diffraction (XRD) graph of the composition prepared as per example 01

FIG. 2: X-ray diffraction (XRD) graph of the composition prepared as per example 02

FIG. 3: X-ray diffraction (XRD) graph of the composition prepared as per example 03

FIG. 4: X-ray diffraction (XRD) graph of the composition prepared as per example 04

FIG. 5. Effects of curcumin (Cur) on knee joint protein expression of IL-$\beta$ (A), IL-6 (B), TNF-$\alpha$ (C) and NF-$\kappa\beta$ (D) levels in monosodium iodoacetate (MIA) induced osteoarthritis (OA) rats. The bars point out the standard deviation. Blots were repeated at least three times (n=3) and a representative blot is shown. Asterisks above the lines indicate statistical differences among the groups (ANOVA and Turkey's post-hoc test; P<0.01; *P<0.001; ****P<0.0001). OA, osteoarthritis; Cur, curcumin; MIA, monosodium iodoacetate; IL-1$\beta$, interleukin-1$\beta$; IL-6, interleukin-6; TNF-$\alpha$, tumor necrosis factor $\alpha$; NF-$\kappa\beta$, nuclear factor kappa (3.

FIG. 6. Effects of curcumin (Cur) on knee joint protein expression of collagen type 2 (A), MMP-3 (B), COX-2 (C) and LOX-5 (D) levels in monosodium iodoacetate (MIA) induced osteoarthritis (OA) rats. The bars point out the standard deviation. Blots were repeated at least three times (n=3) and a representative blot is shown. Asterisks above the lines indicate statistical differences among the groups (ANOVA and Turkey's post-hoc test; P<0.01; *P<0.001; ****P<0.0001). OA, osteoarthritis; Cur, curcumin; MIA, monosodium iodoacetate; MMP-3, matrix metalloproteinase-3; COX-2, cyclooxygenase-2; LOX-5, 5-lipoxygenase.

FIG. 7. Effects of curcumin (Cur) on the knee joint in monosodium iodoacetate (MIA) induced osteoarthritis (OA) rats. Representative radiographic images (A) obtained at the end of the experiment are shown. Mean values of Kellgren-Lawrence scores are demonstrated with ±standard deviations (B). Asterisks indicate statical differences of Kellgren-Lawrence scores among the groups represented with bar (Kruskal-Wallis followed by Mann-Whitney U; *P<0.05 **P<0.01; compared as OA group).

FIG. 8. Effects of curcumin (Cur) on histopathology of the knee joint in monosodium iodoacetate (MIA) induced osteoarthritis (OA) rats. Representative histopathologic images of hematoxylin-eosin (A) and toluidin blue (B) staining obtained at the end of the experiment are shown. Mean values of Mankin scores are demonstrated with ±standard deviations. Asterisks above the line indicate statical differences of Mankin scores among the groups represented (C) with bar (Kruskal-Wallis followed by Mann-Whitney U; *P<0.05; compared as OA group).

FIG. 9. Effects of curcumin (Cur) on knee swelling (A), left knee joint diameter (B) right knee joint diameter (C) and the ratio of right to left diameter values (D) in monosodium iodoacetate (MIA) induced osteoarthritis (OA) rats. Asterisks above the lines indicate statistical differences among the groups (ANOVA and Turkey's post-hoc test; P<0.01; *P<0.001; ****P<0.0001).

FIG. 10. Effects of curcumin (Cur) on paw area (B) and stride length (D) in monosodium iodoacetate (MIA) induced osteoarthritis (OA) rats. Representative measures of paw area (A) and stride length (C) are shown. Asterisks above the lines indicate statistical differences among the groups (ANOVA and Turkey's post-hoc test; *P<0.05; P<0.01; *P<0.001; ****P<0.0001).

FIG. 11: Plasma total curcuminoids concentration of Curcumin composition vs Reference

DETAILED DESCRIPTION OF THE PRESENT INVENTION

According to embodiment of the present invention, the stable curcumin formulation comprises curcuminoids in different polymorphic form like amorphous and crystalline in selective ratio for enhancement in bioavailability. According to further embodiment of the present invention the stable curcumin formulation comprising curcuminoids either alone and/or along with at least one excipient to form stable curcumin composition having enhancement in absorption and bioavailability for prevention, improvement and maintenance of arthritis more particularly to osteoarthritis.

Within the context of this invention the terminology the "curcumin composition" is commonly used in the specification to refer composition comprising curcuminoids in different polymorphic form like amorphous and crystalline in selective ratio either alone and/or along with at least one excipient to form stable curcumin composition having enhancement in absorption and bioavailability.

Curcumin (1, 7 bis (4-hydroxy-3-methoxy phenyl)-1, 6 heptadiene-3, 5-dione), is a principal curcuminoid of the popular Indian spice *Curcuma longa* commonly known as turmeric, a perennial herb of Zingiberaceae (ginger) family. It is to be appreciated that the term "curcumin" can be interpreted to be within the scope of the term curcuminoids, which can in general include components of curcumin such as curcumin, demethoxy curcumin and bisdemethoxy curcumin. Commercial products which may be referred to as "curcumin" may have these components, along with other components belonging to the class curcuminoids. The curcumin extract contains total curcuminoids in the range of 40-99%.

According to further embodiment of the present invention the curcumin composition comprising curcuminoids present in the range of 10-90% w/w of the composition.

According to further embodiment of the present invention the stable curcumin formulation comprising curcuminoids either alone and/or along with at least one excipient to form stable curcumin composition having enhancement in absorption and bioavailability. More preferably, stable curcumin composition is formulated using excipients selected from the group of, but not limited to a hydrophilic carrier, an antioxidant, solvent, emulsifier, surfactant, solubilizer, stabilizer, pH modifier, binder, anticaking agent, fat and/or the combination thereof.

In one more embodiment, the solid hydrophilic carrier employed in preparation of curcumin compositions is selected from the group such as, but not limited to, cellulose derivatives, polyacrylates, polyethylene glycols, povidones, starch and starch derivatives, gums, sugars, pectin, plant polysaccharides, protein such as casein, whey protein, soy protein, pea protein, sugar alcohol, glucose, polyvinyl pyrrolidone, and the like.

According to preferred embodiment the hydrophilic carrier is Hydroxypropyl methyl cellulose.

According to further embodiment, the hydrophilic carrier is present in the range of 1-90% w/w of the composition.

In one more embodiment, the antioxidant in preparation of curcumin compositions is selected from the group such as, but not limited to natural tocopherols, mixed tocopherol, ascorbyl palmitate, rosemary extract, epigallocatechin gallate, catechins, and ascorbic acid.

According to further embodiment, the antioxidant is present in the range of 0.1-10% w/w of the composition.

In one more embodiment, the solvent in preparation of stable curcumin composition is selected from the group such as, but not limited to, isopropyl alcohol, acetone, methanol, alcohol, ethyl acetate, ethanol, methylene dichloride, water and mixtures thereof. The temperature maintained for obtaining a homogenous mass may range from ambient to 80° C.; preferably 25° C. to 60° C.

According to further embodiment, the solvent is present in the range of 40-98% w/w of the composition.

In one more embodiment, the emulsifier in preparation of stable curcumin composition is selected from the group such as, but not limited to polysorbate, sugar alcohols, glycerol & derivatives thereof.

According to further embodiment, the emulsifier is present in the range of 0.1-10% w/w of the composition.

In one more embodiment, the surfactant in preparation of stable curcumin composition is selected from the group such as, but not limited to sugar alcohols, sugar esters (such as sucrose stearate and others), esters of sugar alcohol (such as sorbitan and others) According to further embodiment, the surfactant is present in the range of 0.1-10% w/w of the composition.

In one more embodiment, the solubilizer in preparation of curcumin compositions is selected from the group such as, but not limited to propylene glycol alginate, sugar alcohols, sugar esters, phospholipid, Lecithin, d-limonene, Vitamin E TPGS (d-α-Tocopheryl polyethylene glycol 1000 succinate), sodium lauryl sulphate and beta cyclodextrin.

According to further embodiment, the solubilizer is present in the range of 0.1-40% w/w of the composition.

In one more embodiment, the stabilizer in preparation of curcumin compositions is selected from the group such as, but not limited to glyceryl monostearate, sugar alcohols, triglycerides, antioxidants, monoglycerides and phospholipids.

According to further embodiment, the stabilizer is present in the range of 0.1-10% w/w of the composition.

In one more embodiment, the pH modifier in preparation of curcumin compositions is selected from the group such as, but not limited to citric acid, trisodium citrate, lactic acid, L-arginine, calcium carbonate and magnesium carbonate.

According to further embodiment, the pH modifier is present in the range of 0.1-10% w/w of the composition.

In one more embodiment, the binder in preparation of curcumin compositions is selected from the group such as, but not limited to hydroxy propyl cellulose, pregelatinized and starch.

According to further embodiment, the binder is present in the range of 0.1-10% w/w of the composition.

In one more embodiment, the anticaking agent in preparation of curcumin compositions is selected from the group such as, but not limited to colloidal silicon dioxide, magnesium stearate, stearic acid, and mannitol.

According to further embodiment, the anticaking agent is present in the range of 0.1-10% w/w of the composition.

In one more embodiment, the fat employed in preparation of curcumin compositions is selected from the group such as, but not limited to, medium chain triglycerides, long chain triglycerides, vegetable oils, esters of fatty acids, hydrocarbons such as terpenes, monoglycerides According to further embodiment, the fat is present in the range of 0.1-40% w/w of the composition.

According to further embodiment of the present invention stable curcumin composition described herein exhibit enhanced bioavailability and the compositions can be available in orally administrable solid, semisolid, liquid forms, selected from, but not limited to dosages such as, powders, granules, pellets, beadlets, caplets, tablets, capsules, soft gel capsules, solution, emulsions, suspensions, dispersions and the like.

According to one more embodiment of the present invention the curcumin composition is in the form of granule.

According to one more embodiment of the present invention the curcumin composition is in the form of powder.

In some embodiment, a process for the preparation of a stable curcumin composition having enhancement in stability and bioavailability use for osteoarthritis comprises:

(i) Dissolving one or more excipients in solvent or mixture thereof with continue stirring for 10-15 min at 50-80° C.;

(ii) Dissolving curcumin in solvent or mixture thereof with continue stirring for 5-10 min at 50-80° C. followed by cool down to temperature to 30-40° C.; and (iii) adding, other excipients such as hydrophilic carrier, an antioxidant, diluents, stabilizer, pH modifier, anticaking agent, fat, emulsifier and surfactant, in a solvent to form a homogenous mass;

(iv) removing the solvent by evaporation to form a dry mass; and (v) pulverizing the dry mass to form a fine powder.

The removal of solvent in step (ii) can be performed in vacuum distillation or evaporation technique, or by spray drying technique. The resultant dry mass is pulverized by using, for example, mortar and pestle, mixer-grinder, multimill, ball mill, jet mill and the like.

According to further embodiment of the present invention provides the stable curcumin composition is use for prevention, improvement and maintenance of arthritis more specifically osteoarthritis.

According to further embodiment of the present invention provides the stable curcumin composition is use for prevention, improvement and maintenance of osteoarthritis.

According to further embodiment of the present invention provides the stable curcumin composition is used for maintenance of Joint wellness.

According to further embodiment of the present invention provides the stable curcumin which exhibits increased joint mobility, comfortable movements for ease of daily activities, improve walking performance, increased joint flexibility, reduction in joint stiffness, reduced joint discomfort/pain, reduced inflammation and reduced cartilage breakdown.

According to further embodiment of the present invention the stable curcumin composition uses for improvement in muscle strength and muscle performance, reduction in muscle soreness and muscle damage and promote faster muscle recovery.

Example 01

| Sr. No. | Ingredient | % w/w |
|---|---|---|
| 1 | Curcumin Extract | 24 |
| 2 | Hydroxypropyl methyl cellulose | 67.1 |
| 3 | Lecithin | 2 |
| 4 | Medium Chain Triglyceride (MCT Oil) | 1 |
| 5 | Glyceryl Monostearate | 0.5 |
| 6 | Citric acid anhydrous | 0.5 |
| 7 | Mixed Tocopherol | 0.5 |
| 8 | Silicon Dioxide | 0.5 |
| 9 | d-limonene | 2 |
| 10 | Sodium Lauryl Sulphate | 1.9 |
| 11 | IPA | 190 |
| 12 | MDC | 760 |
| | Total(solid content) | 100 |

(Total Curcuminoids. in %) = Qty. of extract (in %)* strength of extract (% Curcuminoids)/ 100 = 24*95/100 = 22.8%

The process for preparation of composition has defined in the stepwise manner as follows:

i) Dissolve Citric Acid anhydrous, Glyceryl monostearate, Lecithin in mixture of Isopropyl alcohol & Methylene Dichloride under heating at 55-60° C. Add curcumin extract containing from curcumin, demethoxy curcumin and bisdemethoxy curcumin under heating at 55-60° C. and stir for 25-40 min until dissolve completely. The above solution was cooled down to 30-40° C.

ii) Further add hydroxypropyl methylcellulose and sodium lauryl sulphate under stirring condition.

iii) Add Medium Chain Triglyceride oil, d-limonene and Tocopherol in step (ii) solution under stirring. The solution was stirred for 35-45 min to obtain homogeneous solution.

iv) The homogeneous solution was used as feed liquid for spray dryer. The powder obtained from spray dryer was further dried in vacuum dryer at temperature 50-90° C. which is then sifted and blended after adding colloidal silicon dioxide. The product obtained was yellowish orange free flowing homogeneous powder.

v) FIG. 01 shows the X-ray powder diffraction (XRD) of the curcumin composition having 1.2% of crystalline polymorph and 98.8% of the amorphous polymorph of the curcuminoid.

Example 02

| Sr. No | Ingredient | % w/w |
|---|---|---|
| 1 | Curcumin Extract | 24.0 |
| 2 | Mixed Tocopherol | 0.5 |
| 3 | Hydroxypropyl Methylcellose | 67.1 |
| 4 | Citric Acid anhydrous | 1.5 |
| 5 | Lecithin | 4.9 |
| 6 | Medium Chain Triglycerides (MCT Oil) | 1.0 |
| 7 | Glyceryl monostearate | 0.5 |
| 8 | Colloidal Silicon Dioxide | 0.5 |

-continued

| Sr. No | Ingredient | % w/w |
|---|---|---|
| 9 | Isopropyl alcohol | 190 |
| 10 | Methylene Dichloride | 760 |
| | Total (Solid content) | 100 |

(Total Curcuminoids. in %) = Qty. of extract (in %)* strength of extract (% Curcuminoids)/ 100 = 24*95/100 = 22.8%

The process for preparation of composition has defined in the stepwise manner as follows:

i) Dissolve Citric Acid anhydrous, Glyceryl monostearate, Lecithin in mixture of Isopropyl alcohol & Methylene Dichloride under heating at 55-60° C. Add curcumin extract containing from curcumin, demethoxy curcumin and bisdemethoxy curcumin under heating at 55-60° C. and stir for 25-40 min until dissolve completely. The above solution was cooled down to 30-40° C.

ii) Further add hydroxypropyl methylcellulose under stirring condition.

iii) Add Medium Chain Triglyceride oil and Tocopherol in step (ii) solution under stirring. The solution was stirred for 35-45 min to obtain homogeneous solution.

iv) The homogeneous solution was used as feed liquid for spray dryer. The powder obtained from spray dryer was further dried in vacuum dryer at temperature 50-90° C. which is then sifted and blended after adding colloidal silicon dioxide. The product obtained was yellowish orange free flowing homogeneous powder.

v) FIG. 02 shows the X-ray powder diffraction (XRD) of the curcumin composition having 1.2% of crystalline polymorph and 98.8% of the amorphous polymorph of the curcuminoid.

Example 03

| Sr. No. | Ingredient | % w/w |
|---|---|---|
| 1 | Curcumin Ext | 24 |
| 2 | Hydroxypropyl methyl cellulose | 69 |
| 3 | Lecithin | 2 |
| 4 | Medium Chain Triglyceride (MCT Oil) | 1 |
| 5 | Glyceryl Monostearate | 0.5 |
| 6 | Citric acid anhydrous | 0.5 |
| 7 | d-limonene | 2 |
| 8 | Mixed Tocopherol | 0.5 |
| 9 | Silicon Dioxide | 0.5 |
| 10 | Ethanol | 240 |
| 11 | Ethyl acetate | 960 |

(Total Curcuminoids. in %) = Qty. of extract (in %)* strength of extract (% Curcuminoids)/ 100 = 24*95/100 = 22.8% i) Dissolve Citric Acid anhydrous, Glyceryl monostearate, Lecithin in mixture of ethanol and ethyl acetate under heating at 55-60° C. Add curcumin extract under heating at 55-60° C. and stir for 25-40 min until dissolve completely. The above solution was cooled down to 30-40° C.

ii) Further add hydroxypropyl methylcellulose under stirring condition.

iii) Add Medium Chain Triglyceride oil, d-limonene and Tocopherol in step (ii) solution under stirring. The solution was stirred for 35-45 min to obtain homogeneous solution.

iv) The homogeneous solution was used as feed liquid for spray dryer. The powder obtained from spray dryer was further dried in vacuum dryer at temperature 50-90° C. which is then sifted and blended after adding colloidal silicon dioxide. The product obtained was yellowish orange free flowing homogeneous powder.

v) FIG. 03 shows the X-ray powder diffraction (XRD) of the curcumin composition having 2% of crystalline polymorph and 98% of the amorphous polymorph of the curcuminoid.

Example 04

| Sr. No. | Ingredient | % w/w |
|---|---|---|
| 1 | Curcumin Ext | 71.15 |
| 2 | Hydroxypropyl methyl cellulose | 21.25 |
| 3 | Lecithin | 4.6 |
| 4 | Medium Chain Triglyceride (MCT Oil) | 1 |
| 5 | Glyceryl Monostearate | 0.5 |
| 6 | Citric acid anhydrous | 0.5 |
| 7 | Mixed Tocopherol | 0.5 |
| 8 | Silicon Dioxide | 0.5 |
| 9 | Ethanol | 300 |
| 10 | Ethyl acetate | 900 |
| 11 | Water | 200 |

(Total Curcuminoids, in %) = Qty. of extract (in %)* strength of extract (% Curcuminoids)/100 = 71.15*90/100 = 64.04% i) Dissolve Citric Acid anhydrous, Glyceryl monostearate, Lecithin in mixture of ethanol and ethyl acetate under heating at 55-60° C. Add curcumin extract under heating at 55-60° C. and stir for 25-40 min until dissolve completely. The above solution was cooled down to 30-40° C.

ii) Further add hydroxypropyl methylcellulose under stirring condition.

iii) Add Medium Chain Triglyceride oil and Tocopherol in step (ii) solution under stirring. The solution was stirred for 35-45 min to obtain homogeneous solution.

iv) The homogeneous solution was used as feed liquid for spray dryer. The powder obtained from spray dryer was further dried in vacuum dryer at temperature 50-90° C. which is then sifted and blended after adding colloidal silicon dioxide. The product obtained was yellowish orange free flowing homogeneous powder.

v) FIG. 04 shows the X-ray powder diffraction (XRD) of the curcumin composition having 4% of crystalline polymorph and 96% of the amorphous polymorph of the curcuminoid.

Example 05

| Sr. No | Ingredient | % w/w |
|---|---|---|
| 1 | Curcumin Extract | 86.5 |
| 2 | Mixed Tocopherol | 0.5 |
| 3 | Hydroxypropyl Methylcellose | 7 |
| 4 | Citric Acid anhydrous | 0.5 |
| 5 | Lecithin | 4 |
| 6 | Medium Chain Triglycerides (MCT Oil) | 0.5 |
| 7 | Glyceryl monostearate | 0.5 |

-continued

| Sr. No | Ingredient | % w/w |
|---|---|---|
| 8 | Colloidal Silicon Dioxide | 0.5 |
| 9 | Isopropyl alcohol | 380 |
| 10 | Methylene Dichloride | 1520 |
| | Total (Solid content) | 100 |

(Total Curcuminoids, in %) = Qty. of extract (in %)* strength of extract (% Curcuminoids)/100 = 86.5*95/100 = 82.18% i) Dissolve Citric Acid anhydrous, Glyceryl monostearate, Lecithin in mixture of ethanol and ethyl acetate under heating at 55-60° C. Add curcumin extract under heating at 55-60° C. and stir for 25-40 min until dissolve completely. The above solution was cooled down to 30-40° C.

ii) Further add hydroxypropyl methylcellulose under stirring condition.

iii) Add Medium Chain Triglyceride oil, d-limonene and Tocopherol in step (ii) solution under stirring. The solution was stirred for 35-45 min to obtain homogeneous solution.

iv) The homogeneous solution was used as feed liquid for spray dryer. The powder obtained from spray dryer was further dried in vacuum dryer at temperature 50-90° C. which is then sifted and blended after adding colloidal silicon dioxide. The product obtained was yellowish orange free flowing homogeneous powder.

At the outset of the description that follows, it is to be understood that the ensuing description only illustrates a particular form of this invention. However, such a particular form is only an exemplary embodiment and is not intended to be taken restrictively to imply any limitation on the scope of the present invention.

Clinical Experimentation Study 1:

Objective: The present study has been assessed for the efficacy of curcumin composition (test product) in a monosodium iodoacetate (MIA) induced osteoarthritis.

Test product: The curcumin composition comprising of curcuminoids manufactured by OmniActive Health Technologies Limited, India.

Dose 1: 100 mg/kg of formulation (20 mg/kg of total curcuminoids) (Example 1: 1.2% of crystalline polymorph and 98.8% of the amorphous polymorph of the curcuminoid)

Dose 2: 200 mg/kg of formulation (40 mg/kg of total curcuminoids) (Example 1: 1.2% of crystalline polymorph and 98.8% of the amorphous polymorph of the curcuminoid)

Experimental Design: Female wistar rats (8 weeks) randomly allocated into groups as defined below (n=7 in each):

I. Normal Control group

II. Osteoarthritis group

III. Osteoarthritis, curcumin composition dose1 (100 mg/kg of formulation) group and IV. Osteoarthritis, curcumin composition dose2 (200 mg/kg of formulation) group.

In order to induce osteoarthritis in rat model, the right knee of the rats was shaved and disinfected with 70% alcohol following anaesthetization using with xylazine (10 mg/kg) and ketamine hydrochloride (50 mg/kg). 3 mg of MIA was dissolved in 50 μL saline and injected into right knee joints through the infrapatellar ligament using a 0.3 ml insulin syringe fitted with a 29-G needle. Control group was given an injection of 50 μL saline. Two weeks after injection with MIA, the formulation 1 and formulation 2 were dissolved in 1 mL saline given orally for 4 weeks. All rats were observed every other alternate day to assess knee joint swelling.

Four weeks after the rats were sacrificed, and blood and the specimens of the knee joint was collected for the follow-up experiment. The blood samples were centrifuged at 3,000 rpm for 10 min, and the harvested sera was kept at −20° C. until the day of analysis.

Sample Preparation:

Curcumin compositions according to the present invention are as follows:

The test sample for 100 mg/kg & 200 mg/kg has prepared as per the example 1 with the process parameters provided.

Biochemical Analysis

Serum of MDA (malondialdehyde) was analysed by HPLC. Antioxidant enzymes (SOD, CAT, GSHPx), IL-1β, IL-6, IL-10, and TNF-α were measured using the relevant commercial kits according to the enzyme-linked immunosorbent assay (ELISA) method.

Western Blot Analysis

Articular cartilage samples were analysed for the expression of TNF-α, IL-6, IL-1β, nuclear factor kappa B, cyclooxygenase-2 (COX-2), collagen type2, CRP, 5-LOX, MMP3, Cartilage oligomeric matrix protein (COMP) using the Western blot technique.

Histological Analysis

Histological changes were assessed to confirm the effects of product on cartilage degeneration in the knee joints of MIA-induced osteoarthritis rats. Following the rat sacrifice, each knee joint was fixed in 10% formalin for 24 h at 4° C., and decalcified with 5% hydrochloric acid for 4 days at 4° C. Following decalcification specimens were dehydrated in graded acetone and embedded in paraffin. Sections (thickness, 2-3 μm) were stained with 0.2% hematoxylin and 1% eosin for 5 min and 3 min, respectively. The histological preparations were analysed and photographed with a microscope using a digital image capture camera.

Example 1

The objective of the study was to demonstrate the effect of curcumin composition as per this invention on serum inflammation markers.

Method: Animals were sacrificed, and serum samples collected and assessed for serum biomarkers measured using the relevant commercial kits according to the enzyme-linked immunosorbent assay (ELISA) method as shown in the table 1 and illustratively provided in FIG. 5.

TABLE 01

| Marker | Control | OA | OA + Curl | OA + Cur2 | —P—* |
|---|---|---|---|---|---|
| | | | Groups | | |
| TNF-α, pg/mL | $21.29 \pm 3.14^d$ | $72.05 \pm 8.61^a$ | $55.48 \pm 7.93^b$ | $43.71 \pm 6.90^c$ | 0.0001 |
| IL-1β, pg/mL | $18.61 \pm 1.67^d$ | $54.79 \pm 4.64^a$ | $41.03 \pm 2.96^b$ | $31.96 \pm 2.62^c$ | 0.0001 |
| IL-6, pg/mL | $10.58 \pm 1.02^d$ | $63.93 \pm 5.38^a$ | $48.40 \pm 3.91^b$ | $36.93 \pm 2.90^c$ | 0.0001 |
| IL-10, pg/mL | $98.12 \pm 6.33^a$ | $34.06 \pm 2.61^d$ | $47.58 \pm 4.12^c$ | $57.09 \pm 6.39^b$ | 0.0001 |
| COMP, ng/mL | $7.77 \pm 0.88^d$ | $27.68 \pm 2.99^a$ | $20.11 \pm 2.08^b$ | $14.44 \pm 1.98^c$ | 0.0001 |
| CRP, mg/L | $1.25 \pm 0.33^d$ | $11.27 \pm 1.55^a$ | $5.81 \pm 0.70^b$ | $4.21 \pm 0.84^c$ | 0.0001 |

Abbreviations:
OA: Osteoarthritis group
Curl: Curcumin composition dose 1 (100 mg/kg of formulation)
Cur2: Curcumin composition dose 2 (200 mg/kg of formulation)
TNF-α: tumor necrosis factor α;
IL-1β: interleukin-1β;
IL-6: interleukin-6;
IL-10: interleukin-10;
COMP: cartilage oligometrix matrix protein;
CRP: c-reactive protein.
Statistical comparisons are indicated with different superscript (a-d) in the same row (P < 0.05;
*ANOVA and Turkey's post-hoc test). Mean values of items are demonstrated with ± standard deviations.

Conclusion:

From the table 1 and FIG. 5, it was observed that serum inflammatory markers such as TNFα, IL1β, IL-6, COMP, CRP which are responsible for induction of inflammation and associated pathology were increased during OA and treatment with curcumin composition 1 and curcumin composition 2 reduced these levels in a statistically significant manner. Levels of cytokine IL-10 reduced during OA were restored by treatment.

Example 2

The objective of the study was to demonstrate effect of curcumin composition on serum antioxidant markers.

Method: Animals were sacrificed, and serum samples collected and assessed for serum antioxidant markers. Serum of MDA was analyzed by HPLC. Antioxidant enzymes (SOD, CAT, GSHPx) were measured using the relevant commercial kits according to the enzyme-linked immunosorbent assay (ELISA) method and data shown in the table below.

TABLE 02

| Marker | Control | OA | OA + Curl | OA + Cur2 | —P—* |
|---|---|---|---|---|---|
| | | | Groups | | |
| MDA, nmol/mL | $0.63 \pm 0.07^d$ | $1.97 \pm 0.08^a$ | $1.65 \pm 0.09^b$ | $1.19 \pm 0.18^c$ | 0.0001 |
| SOD, U/mL | $50.45 \pm 4.07^a$ | $21.86 \pm 3.43^d$ | $31.35 \pm 2.35^c$ | $38.03 \pm 3.59^b$ | 0.0001 |

TABLE 02-continued

| Marker | Control | OA | OA + Cur1 | OA + Cur2 | —P—* |
|--------|---------|-----|-----------|-----------|------|
| | | Groups | | | |
| CAT, U/mL | $142.68 \pm 6.58^a$ | $60.64 \pm 7.48^d$ | $71.76 \pm 5.74^c$ | $89.77 \pm 6.05^b$ | 0.0001 |
| GSH-Px, U/mL | $117.94 \pm 5.68^a$ | $59.82 \pm 3.32^c$ | $63.78 \pm 6.69^c$ | $85.84 \pm 4.98^b$ | 0.0001 |

MDA: malondialdehyde;
SOD: superoxide dismutase;
GSH-Px: glutathione peroxidase;
CAT: catalase.
Statistical comparisons are indicated with different superscript (a-d) in the same row (P < 0.05; *ANOVA and Turkey's post-hoc test). Mean values of markers are demonstrated with ± standard deviations Conclusion:

MDA which is a marker of oxidative stress that plays a key role in induction of pathology of OA was significantly increased during OA and were significantly reduced during treatment. Similarly, treatment significantly improved the levels of antioxidant enzymes, SOD, CAT and GSH-Px as shown in the table 2.

Example 3

The objective of the study was to demonstrate effect of curcumin composition on inflammation markers in synovial joint tissue.

Method: Animals were sacrificed, and synovial tissue samples collected and assessed for inflammatory markers by western blot as shown in FIG. 05.

Conclusion:

It was observed that protein levels of inflammatory markers as shown below; IL-β (A), IL-6 (B), TNF-α (C) and NF-κβ (D) were increased in OA rats as measured by western blot followed by densitometric analysis of the relative intensity according to the control group after (β-actin normalization to ensure equal protein loading. Blots were repeated at least three times (n=3) and a representative blot (E) is shown.

It was observed that treatment with curcumin composition at two doses (100 & 200 mg/kg) reduced the levels of inflammatory markers in the joint tissue in a statistically significant manner.

Example 4

The objective of the study was to demonstrate effect of curcumin composition on cartilage degradation and inflammation markers in synovial joint tissue.

Method: Animals were sacrificed, and synovial tissue samples collected and assessed for markers of cartilage degradation and inflammation by western blot as shown in FIG. 06.

Conclusion:

It was observed that protein levels of markers of collagen degradation such as Collagen Type 2 (A), MMP-3 (B) and inflammatory markers COX-2 (C) and LOX-5 (D) shown below were increased in OA rats as measured by western blot followed by densitometric analysis of the relative intensity according to the control group after (3-actin normalization to ensure equal protein loading. Blots were repeated at least three times (n=3) and a representative blot (E) is shown.

It was observed that treatment with curcumin composition at two doses reduced the levels of markers of cartilage degradation and inflammation in the joint tissue in a statistically significant manner Example 5

The objective of the study was to demonstrate effect of curcumin composition on joint architecture of synovial joint as assessed by X-ray image analysis Method: Animals were evaluated for structural integrity of synovial joint by radiography analysis as shown in FIG. 07 and table 04.

TABLE 4

| Stage | Radiologic Findings |
|-------|---------------------|
| | Kellgren-Lawrence scoring system (Kellgren and Lawrence, 1957). |
| 0 | None |
| 1 | Doubtful: Suspicious narrowing of the joint space and possible osteophyte formation. |
| 2 | Minimal: Definite osteophyte and possible narrowing of the joint space. |
| 3 | Moderate: Numerous moderate osteophytes, definite narrowing of the joint space, some sclerosis and possible deformity of the bone ends. |
| 4 | Severe: Large osteophytes, marked narrowing of the joint space, sclerosis and deformity of the bone ends |

Conclusion:

It was observed that induction of OA is associated with loss of joint structural integrity as observed by radiographic images (A) obtained at the end of the experiment. Significant improvement in the joint architecture was observed after treatment with curcumin composition 1 & curcumin composition 2. The above results were further validated by measuring mean values of Kellgren-Lawrence scores (B) with ±standard deviations.

Example 6

The objective of the study was to demonstrate effect of curcumin composition on morphological analysis of synovial joint tissue.

Method: Animals were sacrificed, and synovial tissue samples collected, fixed in 10% formalin for 24 h at 4° C., decalcified with 5% hydrochloric acid for 4 days at 4° C., dehydrated in graded acetone and embedded in paraffin. Sections of 2-3 μm thickness were stained with 0.2% hematoxylin and 1% eosin for 5 min and 3 min, respectively and histological preparations were analyzed and photographed with a microscope using a digital image capture camera as shown in FIG. 8.

Conclusion:

It was observed that there was a significant loss of joint structure and inflammatory infiltration of joint in OA condition as observed after histopathologic images of hematoxylin-eosin (A) and toluidine blue (B) staining obtained at the end of the experiment. This was further validated by mean values of Mankin scores (C).

Example 7

The objective of the study was to demonstrate effect of curcumin composition on morphological analysis of synovial joint tissue.

Method: Knee was visually assessed for morphological changes of joint pathology such as knee swelling, knee joint diameter, and ratio of right to left diameter values as shown in FIG. 09.

Conclusion:

Both right and left knee joint swelling was observed when OA was induced in rats and this was significantly reduced by treatment with curcumin composition 1 and curcumin composition 2 (A). This was further validated by measuring left knee joint diameter (B) right knee joint diameter (C) and the ratio of right to left diameter values and a significant treatment effect was observed with curcumin composition 1 & curcumin composition 2.

Example 8

The objective of the study was to demonstrate effect of curcumin composition on paw area and stride length.

Method: The hind paws of rats were brushed with ink and the animals were allowed to run on a 60 cm-long, 7 cm-wide track covered with white paper. A dark chamber was placed at the end of the track to entice rats. Upon completion of the test, the paper was scanned at 300 dpi. The measurement around the paw was defined as paw area (cm2), the distance between the first and fifth toes as paw width (cm), the distance of the same hind paw between two steps as stride length (cm), the horizontal distance between the left and right paw as the base (cm), the distance between the third toe and the heel as paw length (cm) and the paw angle as the angle through the hind legs (°). The measures of footsteps were quantified by ImageJ software as shown in FIG. 10.

Conclusion:

Paw area and stride length were significantly reduced due to osteoarthritis. There was a significant improvement in both paw area and stride length with curcumin composition 1 and curcumin composition 2.

Clinical Experimentation Study 2:

Objective: The purpose of this study was to evaluate the plasma pharmacokinetic profile of the curcumin composition in adult Male Sprague Dawley.

Dose Selection

The dose of 1000 mg/kg body weight (200 mg/kg of total curcuminoids) was selected for oral route of administration.

Test product: Curcumin composition as per example 01

Reference: Curcumin extract (Curcumin extract without any formulation and polymorphic form) Curcumin extract (Regular Curcumin) extract without any formulation and polymorphic in general prepared by thing turmeric rhizome extracted with solvent and evaporated to form oleoresin turmeric which further oleoresin crystallized using suitable solvent. The obtained crystals are dried and powdered which contain 95% of curcuminoids Time point (hr.): 0.00, 0.25, 0.50, 1.00, 2.00, 3.00, 4.00, 6.00, 8.00 and 24.00

TABLE 05

| Parameters | Reference Mean ± SD | Curcumin composition 20% Mean ± SD | Fold increase of Curcumin composition 20% over Reference |
|---|---|---|---|
| Cmax (ng/mL) | 28.169 ± 28.604 | 1522.184 ± 257.839 | 54.04X |
| Tmax (h) | 0.656 ± 0.719 | 1.938 ± 0.863 | 2.95X |
| AUClast (hr*ng/mL) | 95.349 ± 55.134 | 6170.474 ± 1071.967 | 64.71X |
| $t^{1/2}$ (h) | 2.19 ± 0.81 | 5.103 ± 0.725 | 2.33X |

Cmax: Peak plasma concentration

Tmax: Time to reach the peak plasma concentration $AUC_{0-last}$: Area under the concentration-time curve from time zero to last quantifiable concentration $t_{1/2}$: Half-life Conclusion:

Curcumin composition showed 64.71 folds higher AUC compared to reference curcumin extract. Based on the results and conclusions provided on osteoarthritis model, we here by concluded that the same curcumin composition will also have a beneficial effect on muscle health. The cell line study model with further evidenced by the study protocol has been illustrated below to study the efficacy on muscle health.

Further study to demonstrate the effect of curcumin composition on muscle health as follows.

In-Vitro Study:

Objective: Demonstration of ergogenic potential curcumin composition (test product) for improving physiological or metabolic responses that may help in muscle development (prevent loss of muscle protein as in age-related sarcopenia), enhance exercise performance, ameliorate muscle injury and muscle inflammation (DOMS)

Cell model: C2C12 murine myoblasts

Experimental approaches: As per the studies were conducted on basic assays and generate more information after we identify selected ingredients for development C2C12 myoblasts was cultured at 37° C. in humidified 5% CO2 were plated in 24 well-plate and incubated for 24h before adding treatment 1. Cytotoxicity assay
2. Mitochondrial density assay: Effect of ingredients on mitochondrial biogenesis is analyzed by measuring cellular respirations accompanied by increase in mitochondrial mass is calculated.
3. Antioxidant Capacity: After 24h of treatment, the total antioxidant capacity was determined in C2C12 homogenates
4. Lactate dehydrogenase and Creatine Kinase activity: LDH and CK activities are used as indicator of the occurrence of muscle cell damage and is assessed by determining the release of the cytosolic enzyme lactate dehydrogenase (LDH) and creatine kinase (CK) activity
5. IGF-1 Elisa assay: IGF-I exerts acute anabolic actions on protein and carbohydrate metabolism by increasing the cellular uptake of amino acids in cells and plays a major role in the regulation of skeletal muscle growth.

In-Vivo Study:

Objective: To evaluate the effect of curcumin composition (test product) formulation on endurance, grip strength and muscle metabolism in rats.

Animals and Experimental Design:

21 Wistar Albino or Sprague Dawley male rats (20% extra animals), age: 8 weeks, weight: 180±20 g were housed in a controlled environment with a 12:12-h light-dark cycle at 22° C. and were provided with rat chow and water ad libitum.

Rats were randomly divided into 3 treatment groups, each containing 7 animals.

1. Control (Normal and exercised)
2. Curcumin composition 1 (100 mg/kg of formulation)
3. Curcumin composition 2 (200 mg/kg of formulation)

At screening period, the grip strength was performed on day 3. On day −2, Treadmill Test will be performed.

Grip Strength Test:

The grip strength of the rats was evaluated using a force measurement system. Combined forelimb and hind limb grip strength and forelimb grip strength were measured at the end of the oral administration period. The system has an electronic digital force gauge that determines the peak force. Each rat was held by the tail until it released the pull bar. Five consecutive tests were performed on each rat to obtain the peak value.

Treadmill Test:

An animal treadmill was used to measure the running endurance of the rats. The rats were subjected to overnight fasting and sacrificed by cervical dislocation and blood and gastrocnemius muscle were collected. Serum samples was obtained by taking blood samples to gel biochemical tubes after centrifugation (5000 rpm at 4° C. for 10 minutes). Samples of the liver and from the gastrocnemius muscle (taken from approximately the same location each time) was quickly removed, placed on ice, and kept at −80° C. until analyses. For biochemical assays, tissues samples were homogenized within 10 min in 10 volumes of cold Tris 10 mM (pH 7.4). Muscle homogenates was centrifuged at 4000×g at 4° C. for 10 min to yield the low-speed supernatant fraction that was used for the lipid peroxidation analyses.

Biochemical Analysis:

Serum glucose, lipid profile, aspartate aminotransferase (AST), alanine aminotransferase (ALT), urea, creatinine levels will be analyzed with a portable automated chemistry analyzer (Samsung LABGEO PT10V, Samsung Electronics Co., Suwon, Korea). Rat Lactate Assay Kit (Cayman Chemical Co., Ann Arbor, Mich., USA) will be used to measure the serum lactate concentrations through enzyme-linked immunosorbent assays (ELISA, Elx-800, Bio-Tek Instruments Inc, Vermont, USA). ELISA (MyBioSource, San Diego, CA, USA) will also be used in measuring serum myoglobin concentration.

The malondialdehyde (MDA) level in muscle tissue was measured by high-performance liquid chromatography (Shimadzu, Tokyo, Japan) using a Shimadzu UV-vis SPD-10 AVP detector and C18 ODS-3, 5 µm, 4.6 mm×250 mm column. The activities of superoxide dismutase (SOD), catalase (CAT), and glutathione peroxidase (GSH-Px) was determined using commercially available kits (Cayman Chemical, Ann Arbor, MI, USA) according to the manufacturer's procedure.

It has to evident to those skilled in the art that the invention is not limited to the details of the illustrative examples and that the present invention may be embodied in other specific forms without departing from the essential attributes thereof. It is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

We claim:

1. A stable curcumin composition having enhanced bioavailability comprising;
i) curcumin containing (a) crystalline polymorphic form of curcuminoids in a range of 0% to 15% w/w of the total curcuiminoids, and (b) amorphous polymorphic form of curcuminoids in a range of 85% to 100% w/w of the total curcuminoids; and
ii) at least one or more pharmaceutically or nutraceutically acceptable ingredient selected from the group consisting of hydrophilic carrier, antioxidant, stabilizer, pH Modifier, solubilizer, fat, and anticaking agent.

2. The stable curcumin composition as claimed in claim 1, wherein the curcuminoids are selected from the group consisting of curcumin, demethoxycurcumin, bisdemethoxycurcumin, and a mixture thereof.

3. The stable curcumin composition as claimed in claim 1, wherein the curcuminoids are present in a range of 10% w/w of the composition to 90% w/w of the composition.

4. The stable curcumin composition as claimed in claim 1, wherein the composition has increased bioavailability of 60-70 folds against reference.

5. The stable curcumin composition as claimed in claim 1, wherein the hydrophilic carrier is selected from the group consisting of, cellulose, starch, and derivatives thereof, and is present in a range of 1%-90% w/w of the composition.

6. The stable curcumin composition as claimed in claim 1, wherein the antioxidant is selected from the group consisting of tocopherols, mixed tocopherol, ascorbyl palmitate, catechins, and ascorbic acid; and is present in a range of 0.1%-10% w/w of the composition.

7. The stable curcumin composition as claimed in claim 1, wherein the stabilizer is selected from the group consisting of glyceryl mono stearate, sugar alcohols, and triglycerides; and is present in a range of 0.1%-10% w/w of the composition.

8. The stable curcumin composition as claimed in claim 1, wherein the pH Modifier is selected from the group consisting of citric acid, trisodium citrate, lactic acid, and magnesium carbonate; and is present in a range of 0.1%-10% w/w of the composition.

9. The stable curcumin composition as claimed in claim 1, wherein the solubilizer is selected from lecithin, d-limonene, propylene glycol alginate, and sodium lauryl sulphate; and is present in a range of 0.1%-40% w/w of the composition.

10. The stable curcumin composition as claimed in claim 1, wherein the fat is selected from the group consisting of medium chain triglycerides, terpene, and vegetable oil; and is present in a range of 0.1%-40% w/w of the composition.

11. The stable curcumin composition as claimed in claim 1, wherein the anticaking agent is selected from Colloidal Silicon Dioxide, magnesium stearate, steric acid, and mannitol; and is present in a range of 0.1%-10% w/w of the composition.

12. The stable curcumin composition as claimed in claim 1, wherein the composition is in a form selected from the group consisting of tablets, capsules, blended powders, ointments, pastes, lotions, liniments, mouthwashes, gargles, consumable dry syrups, liquid syrups, health drinks, diet drinks, fruit juices, and soft drinks.

13. The stable curcumin composition as claimed in claim 1, wherein the composition is in a form selected from the group consisting of granule, powder, and a mixture thereof.

14. A method for prevention, improvement, and/or maintenance of osteoarthritis in a subject, comprising administering the stable curcumin composition according to claim 1 to a subject in need thereof.

15. A method for improving joint mobility, improving joint flexibility, reducing joint stiffness, improving walking performance, reducing cartilage breakdown, and/or reducing inflammation in a subject, comprising administering the stable curcumin composition according to claim 1 to a subject in need thereof.

16. The method according to claim 14, wherein administering the composition:

(a) decreases one or more inflammatory markers selected from the group consisting of tumor necrosis factor-alpha (TNF-α), interleukin1β (IL-1β), interleukin-6 (IL-6), Collagen Type 2, matrix metalloproteinase-3 (MMP3), cyclooxygenase-2 (COX-2), 5-lipoxygenase (5-LOX), cartilage oligometrix matrix protein (COMP); c-reactive protein (CRP), and malondialdehyde (MDA); and/or (b) increases one or more anti-oxidant markers selected from the group consisting of interleukin-10 (IL-10), superoxide dismutase (SOD), glutathione peroxidase (GSH-Px), and catalase (CAT).

17. A method for improving muscle strength, improving muscle performance, reducing muscle soreness, reducing muscle damage, and/or promoting faster muscle recovery in a subject, comprising administering the stable curcumin composition according to claim 1 to a subject in need thereof.

18. The method according to claim 14, wherein the subject is human and/or animal.

19. The stable curcumin composition as claimed in claim 1 in a dose form, wherein dose is 10-1000 mg/kg.

20. A stable curcumin composition having enhanced bioavailability comprising;

(a) crystalline polymorphic form of curcuminoids in a range of 0% to 15% w/w of the total curcuminoids, and (b) amorphous polymorphic form of curcuminoids in a range of 85% to 100% w/w of the total curcuminoids.

* * * * *